United States Patent
Orlandi

(10) Patent No.: US 9,314,554 B2
(45) Date of Patent: Apr. 19, 2016

(54) IRRIGATION AND SUCTION SYSTEM, IN PARTICULAR FOR LAPAROSCOPIC SURGERY

(75) Inventor: Fabio Orlandi, Milan (IT)

(73) Assignee: AB MEDICA HOLDING S.P.A., Milan (IT)

( * ) Notice: Subject to any disclaimer, the term of this patent is extended or adjusted under 35 U.S.C. 154(b) by 505 days.

(21) Appl. No.: 13/058,185

(22) PCT Filed: Aug. 7, 2009

(86) PCT No.: PCT/IT2009/000375
§ 371 (c)(1),
(2), (4) Date: May 2, 2011

(87) PCT Pub. No.: WO2010/016089
PCT Pub. Date: Feb. 11, 2010

(65) Prior Publication Data
US 2011/0224600 A1    Sep. 15, 2011

(30) Foreign Application Priority Data

Aug. 8, 2008   (IT) ................................ RM08A0447

(51) Int. Cl.
*A61M 1/00*      (2006.01)
*A61M 3/02*      (2006.01)

(52) U.S. Cl.
CPC ........... *A61M 1/0058* (2013.01); *A61M 1/0064* (2013.01); *A61M 3/0258* (2013.01);
(Continued)

(58) Field of Classification Search
CPC .......... A61M 1/0064; A61M 5/14244; A61M 5/14566; A61M 5/16827; A61M 1/267
USPC ............... 604/30, 67, 151–153; 600/188, 560
See application file for complete search history.

(56) References Cited

U.S. PATENT DOCUMENTS 3,508,546 A * 4/1970 Christie et al. .................. 604/27
4,184,510 A * 1/1980 Murry et al. ............. 137/565.23
(Continued)

FOREIGN PATENT DOCUMENTS

WO    WO 98/06446    *   2/1998

OTHER PUBLICATIONS

International Search Report of International Application PCT/IT2009/000375 mailed on Nov. 19, 2010.

*Primary Examiner* — Kami A Bosworth
*Assistant Examiner* — Matthew A Engel
(74) *Attorney, Agent, or Firm* — Lucas & Mercanti, LLP.

(57) ABSTRACT

The present invention concerns an irrigation and suction system, in particular for laparoscopic surgery, comprising an active control apparatus (100), provided with a reusable motor (101') capable to be attached to and to operate a disposable pump (102), and a disposable handpiece (104) provided with two valves (1603, 1604) capable to be connected respectively to an output duct (813) from the pump (102) and to a suction line, the two valves being operatable (1603, 1604) for making respectively the pump (102) and the suction line communicate with an output nozzle (1607) of the handpiece (104), the nozzle (1607) being capable to support a probe (110), the apparatus (100) comprising controlling electronics means (20) for controlling electronics means (1501) for driving the motor (101'), the system being characterised in that it comprises interface means (1505, 16, 17, 112, 113) connected to said controlling electronics means (20) capable to select an operation mode of the motor (101') between continuous mode, wherein the pump (102) delivers fluid in a continuous and uniform way, and pulse mode, wherein the pump flow rate switches between a minimum flow rate and a maximum flow rate with a switching period.

17 Claims, 21 Drawing Sheets

(52) U.S. Cl.
CPC ............... *A61M2205/3331* (2013.01); *A61M 2205/3561* (2013.01); *A61M 2205/3592* (2013.01); *A61M 2205/502* (2013.01)

(56) References Cited

U.S. PATENT DOCUMENTS

| | | | |
|---|---|---|---|
| 4,519,385 A * | 5/1985 | Atkinson et al. | 601/161 |
| 4,561,431 A * | 12/1985 | Atkinson | 601/161 |
| 4,655,197 A * | 4/1987 | Atkinson | 601/161 |
| 4,669,453 A * | 6/1987 | Atkinson et al. | 601/161 |
| 4,803,992 A * | 2/1989 | Lemelson | 600/342 |
| 5,152,746 A * | 10/1992 | Atkinson et al. | 604/31 |
| 5,373,317 A * | 12/1994 | Salvati et al. | 348/65 |
| 5,484,402 A | 1/1996 | Saravia | |
| 5,531,680 A * | 7/1996 | Dumas et al. | 604/67 |
| 5,647,852 A * | 7/1997 | Atkinson | 604/151 |
| 5,879,289 A * | 3/1999 | Yarush et al. | 600/179 |
| 5,993,378 A * | 11/1999 | Lemelson | 600/109 |
| 6,021,341 A * | 2/2000 | Scibilia et al. | 600/407 |
| 6,077,246 A * | 6/2000 | Kullas et al. | 604/151 |
| 6,210,404 B1 * | 4/2001 | Shadduck | 606/34 |
| 6,315,712 B1 * | 11/2001 | Rovegno | 600/109 |
| 6,436,072 B1 * | 8/2002 | Kullas et al. | 604/151 |
| 6,652,453 B2 * | 11/2003 | Smith et al. | 600/188 |
| 6,697,048 B2 * | 2/2004 | Rosenberg et al. | 345/161 |
| 6,929,600 B2 * | 8/2005 | Hill | 600/120 |
| 7,056,123 B2 * | 6/2006 | Gregorio et al. | 434/272 |
| 7,214,213 B2 * | 5/2007 | Michel et al. | 604/207 |
| 7,404,716 B2 * | 7/2008 | Gregorio et al. | 434/272 |
| 8,007,282 B2 * | 8/2011 | Gregorio et al. | 434/272 |
| 8,052,644 B2 * | 11/2011 | Radgowski et al. | 604/151 |
| 8,221,310 B2 * | 7/2012 | Saadat et al. | 600/129 |
| 8,322,365 B2 * | 12/2012 | Wilson et al. | 137/530 |
| 8,323,181 B2 * | 12/2012 | Mukherjee | 600/108 |
| 8,361,041 B2 * | 1/2013 | Fang et al. | 604/264 |
| 8,416,291 B2 * | 4/2013 | Carrey et al. | 348/77 |
| 2003/0078476 A1 * | 4/2003 | Hill | 600/160 |
| 2005/0085690 A1 * | 4/2005 | Tien | 600/109 |
| 2007/0142775 A1 | 6/2007 | Visconti | |
| 2007/0149926 A1 * | 6/2007 | Moberg et al. | 604/152 |
| 2007/0233003 A1 * | 10/2007 | Radgowski et al. | 604/151 |
| 2007/0276183 A1 * | 11/2007 | Melder | 600/112 |
| 2007/0293724 A1 * | 12/2007 | Saadat et al. | 600/156 |
| 2008/0200758 A1 * | 8/2008 | Orbay et al. | 600/112 |
| 2008/0287908 A1 * | 11/2008 | Muni et al. | 604/506 |
| 2010/0004506 A1 * | 1/2010 | Saadat | 600/109 |
| 2010/0063437 A1 * | 3/2010 | Nelson et al. | 604/35 |
| 2010/0137802 A1 * | 6/2010 | Yodfat et al. | 604/152 |
| 2010/0241185 A1 * | 9/2010 | Mahapatra et al. | 607/17 |
| 2010/0256558 A1 * | 10/2010 | Olson et al. | 604/95.01 |
| 2011/0276058 A1 * | 11/2011 | Choi et al. | 606/130 |
| 2012/0174022 A1 * | 7/2012 | Sandhu et al. | 715/781 |
| 2013/0253368 A1 * | 9/2013 | Are et al. | 600/560 |

* cited by examiner

FIG. 19(a)
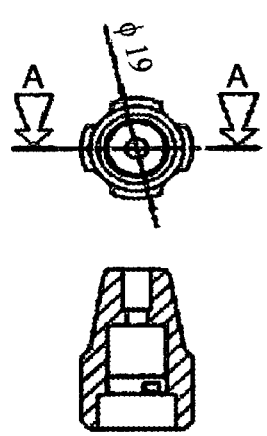
FIG. 19(b)
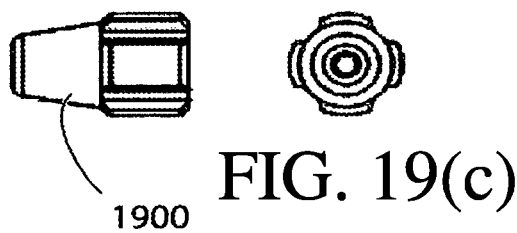
FIG. 19(c)
FIG. 19(d)
sec. A-A

IRRIGATION AND SUCTION SYSTEM, IN PARTICULAR FOR LAPAROSCOPIC SURGERY

CROSS REFERENCE TO RELATED APPLICATIONS

This application is a 371 of International Application No.: PCT/IT2009/000375 filed Aug. 7, 2009, which in turn claims priority under 35 U.S.C. § 119 from Italian Application No.: RM2008A000447 filed Aug. 8, 2008.

BACKGROUND OF THE INVENTION

The present invention relates to an irrigation and suction system, in particular for laparoscopic surgery, that allows in a manner that is reliable, versatile, simple, comfortable for the operator and safe for the patient to carry out a lavage and/or a drainage of the surgical site, in particular during interventions performed by laparoscopy, the system being further capable to be made in an inexpensive way.

It is known that laparoscopic surgery has been widely spread in recent years thanks to its reduced invasivity.

In order to perform an intervention with laparoscopic technique, an apparatus, also called laparoscopic suction irrigator, is used, that comprises, in most advanced configurations, a control base provided with a pumping unit and a handpiece, that has the function of producing an irrigation jet of physiological liquid and carrying out a drainage suction in order to maintain the surgical site view clean during the interventions. The liquid jet and/or the suction occur through a steel probe that is attached to the handpiece and placed by the surgeon close to the intervention location, wherein it is inserted through a device known with the term of "trocar".

The irrigation liquid is drawn from a bag of physiological solution, connected through an infusion line provided with a spike, and it is sent by means of a pump, through an irrigation line, to the probe, that may also operate as suction device depending on specific commands that the surgeon imparts to a valve assembly placed on the handpiece. Depression necessary to aspiration is given by a vacuum line of the operating room, that is connected through disposable collection devices for active drainages.

In the prior art many irrigation and suction systems for laparoscopic surgery are known.

International Application WO 98/03214 concerns a system for irrigating and aspirating from a surgical site, having a pumping unit supplied by a battery and a handpiece.

U.S. Pat. No. 5,303,735 concerns a trumpet valve assembly usable for a surgical irrigation and suction system.

Application EP 1086713 concerns an irrigation and suction system for use during endoscopic surgery, provided with a trumpet valve fed, for irrigation, by a reusable motor to which a disposable sterile pump may be coupled through a quick connection.

U.S. Pat. No. 5,484,402 concerns a surgical irrigation and suction apparatus having a handpiece provided with a control rocking lever.

However, all the irrigation and suction apparatuses of the prior art suffer from some drawbacks.

First of all, they are not much versatile, their dynamic application under variations of surgical conditions being complex and not much reliable.

Moreover, they are uncomfortable to be used by the surgeon, since the means controlling their operation are not easily activatable.

In this context, the solution proposed according to the present invention is introduced, allowing to overcome the aforementioned problems.

It is therefore an object of the present invention to allow in a manner that is reliable, versatile, simple, comfortable for the operator, safe for the patient, and inexpensive to carry out a lavage and/or a drainage of the surgical site, in particular during interventions performed by laparoscopy.

SUMMARY OF THE INVENTION

It is specific subject matter of this invention an irrigation and suction system, in particular for laparoscopic surgery, comprising an active control apparatus, provided with a reusable motor capable to be attached to and to operate a disposable pump, and a disposable handpiece provided with two valves capable to be connected respectively to an output duct from the pump and to a suction line, the two valves being operatable for making respectively the pump and the suction line communicate with an output nozzle of the handpiece, the nozzle being capable to support a probe, the apparatus comprising controlling electronics means for controlling electronics means for driving the motor, the system being characterised in that it comprises interface means connected to said controlling electronics means capable to select an operation mode of the motor between continuous mode, wherein the pump delivers fluid in a continuous and uniform way, and pulse mode, wherein the pump flow rate switches between a minimum flow rate and a maximum flow rate with a switching period.

Always according to the invention, said interface means may be capable to further select a flow rate of the pump and/or, in case of pulse operation, said minimum flow rate and/or said maximum flow rate and/or said switching period.

Still according to the invention, said interface means may comprise a keyboard, preferably along with a display, more preferably along with one or more light signalling LEDs, still more preferably along with an electro-acoustic indicator, or buzzer.

Furthermore according to the invention, said interface means may be housed within the apparatus and/or the handpiece, being connected to said controlling electronics means through a cable or wireless connection, preferably through a radio frequency or infrared connection.

Always according to the invention, the apparatus may comprise detecting, preferably optical, means, connected to said controlling electronics means and capable to detect a priming state of the pump, whereby said controlling electronics means enables or disables said electronics means for driving the motor when said detecting means detects that the pump is, respectively, primed or unprimed.

Still according to the invention, said detecting means may be capable to detect the attaching of a pump to the motor, whereby said controlling electronics means enables or disables said electronics means for driving the motor when said detecting means detects that a pump is, respectively, attached or not attached.

Furthermore according to the invention, said interface means may be further capable to cause an attempt of priming the pump within a maximum period (time-out), whereby the pump is operated for a pre-established period.

Always according to the invention, the apparatus may comprise current detecting means connected to said controlling electronics means capable to detect a current absorbed by the motor, said current detecting means being preferably capable to further detect when said current absorbed by the motor exceeds a maximum threshold value, more preferably directly inhibiting said electronics means for driving the motor.

Furthermore according to the invention, said controlling electronics means may be capable to detect an unpriming state of the pump on the basis of a current absorbed by the motor as detected by said current detecting means, whereby said controlling electronics means enables or inhibits said electronics means for driving the motor when it detects that the pump is respectively primed or unprimed.

Still according to the invention, said controlling electronics means may be capable to detect a number of revolutions of the motor, whereby it inhibits said electronics means for driving the motor when said number of revolutions of the motor is incorrect.

Furthermore according to the invention, the apparatus may comprise watching means connected to said controlling electronics means capable to detect a power-on state of the apparatus and/or malfunctions signalled by said controlling electronics means and/or an insufficient power supply, consequently resetting said controlling electronics means and/or inhibiting said electronics means for driving the motor for at least a time period.

Always according to the invention, the attaching between the motor and the pump may be of coaxial bevel gear pair type, comprising a male driver and a corresponding female driver, preferably according to a labyrinth type geometry seal.

It is still specific subject matter of the present invention an active control apparatus, provided with a reusable motor capable to be attached to and to operate a disposable pump, characterised in that it is used in an irrigation and suction system, in particular for laparoscopic surgery, as previously described, the apparatus comprising controlling electronics means for controlling electronics means for driving the motor connected to interface means capable to select an operation mode of the motor between continuous mode, wherein the pump delivers fluid in a continuous and uniform way, and pulse mode, wherein the pump flow rate switches between a minimum flow rate and a maximum flow rate with a switching period, said interface means being preferably housed at least partially within the apparatus.

It is further specific subject matter of the present invention a handpiece usable in an irrigation and suction system, in particular for laparoscopic surgery, preferably as previously described, comprising an irrigation valve and a suction valve wherein corresponding shutters slide, which shutters are operated respectively by an irrigation button and a suction button for making the respective valves communicate with an output nozzle, the nozzle being preferably capable to be snap-connected through fast coupling to a probe holder, characterised in that the handpiece is ergonomically banana shaped, whereby it allows a comfortable and steady grip by an operator both when it is oriented with the nozzle above the four hand fingers different from the thumb, and when it is oriented in overturned position with the nozzle below such four fingers, the surfaces of the two buttons onto which the fingers of an operator exert a pressure being preferably one convex and the other concave, the handpiece more preferably housing interface means capable to communicate with a control apparatus through a cable and/or wireless connection, still more preferably through a radio frequency or infrared connection.

Always according to the invention, the handpiece may be provided with an anti-skidding coating, preferably in Laprene®, that at least partially covers it.

Still according to the invention, each shutter may be operated by the corresponding button through a respective gear-rack transmission, the buttons and the shutters being provided of end racks engaging two respective gear wheels.

The system according to the invention, made with a reduced number of moving mechanical parts which are hence subject to wear, is extremely reliable and has a long service life. In this regard, in the preferred embodiment, adoption of an electric motor of brushless type allows to eliminate the wear problems of the brushes (proportionally to the operation hours), as well as the physiological dispersion of particles, typically of carbon, removed during rotation phase of the same brushes which, if not well insulated, may be source of serious contamination of the surgical site; moreover, motor shaft is keyed on ball bearings, subject to less wearing rolling friction. The other moving part is a female driver, made of plastic material, directly keyed on the driving shaft, that is therefore not subject to backlashes which could bring the same to "interfere" with the body of the housing. Also, it is not possible that an important wear of the "polygroove" taper hole occurs because it is not possible the motor start without the consent of the sensors checking the complete insertion of the disposable pump and hence of the male driver.

As far as the electronic part is concerned, all power components are oversized with respect to the nominal operation conditions. Moreover, the system is provided with operation controls which avoid transients and excessive loads; in fact, the electronic circuit provides for monitoring of motor power absorption, of acceleration and of reached revolutions compared with the nominal ones at a given power supply condition.

As a consequence, system service life is extremely long even in case of heavy use of the same.

BRIEF DESCRIPTION OF THE DRAWINGS

The present invention will be now described, by way of illustration and not by way of limitation, according to its preferred embodiments, by particularly referring to the Figures of the enclosed drawings, in which:

FIG. 19 shows a top view (FIG. 19a), a side view (FIG. 19b), a bottom view (FIG. 19c), and a cross-section view along the line A-A of FIG. 19a (FIG. 19d) of a probe holder of the system of FIG. 1;

In the Figures, identical reference numbers are used for alike elements.

DETAILED DESCRIPTION

Figure 1:
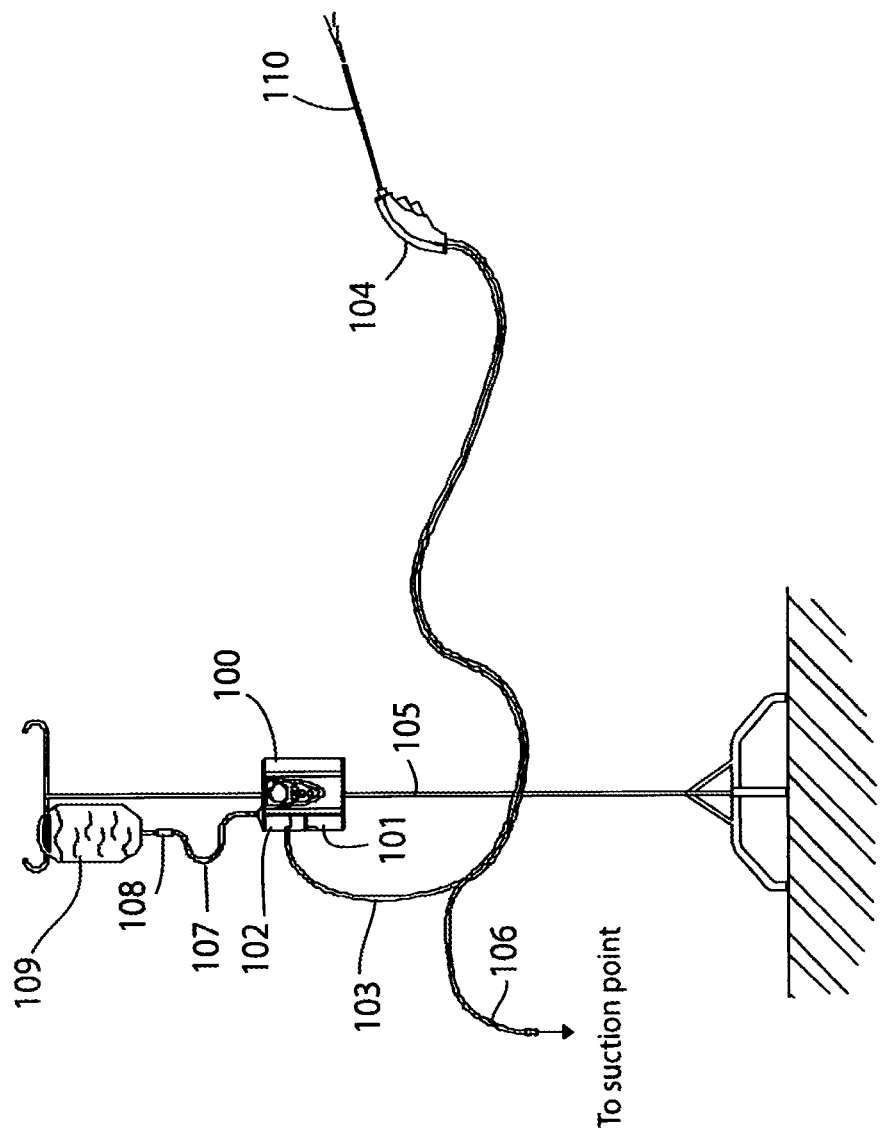
FIG. 1 shows a schematic view of a preferred embodiment of the system according to the invention.

With reference to FIG. 1, it may be observed that the preferred embodiment of the system according to the invention comprises an active control apparatus 100, supplied by the mains (preferably at 230 Vac), provided with a re-usable motor, housed inside a seat 101, on which an extractable disposable centrifugal pump 102 is mounted, connectable through an irrigation pipe 103 to a handpiece 104.

The apparatus 100 is capable to be attached to a normal infusion stand 105 through a rear fastening clamp (illustrated later). A suction pipe 106 is further associated to the irrigation pipe 103 that is also connectable to the handpiece 104 for connecting the latter to a suction point, such as for instance a vacuum line of an operating room, through a disposable collection device for active drainages. The pump 102 is further connectable through an infusion pipe 107 provided with a spike 108 to a bag 109 of liquid, preferably physiological solution, that may be hung on the stand 105.

The handpiece 104 comprises two valves (illustrated later) for manually controlling irrigation and aspiration, and it supports a steel probe 110 that is coupled to a snap fast coupling fastener with which the same handpiece 104 is frontally provided.

The apparatus 100 is a non sterile, reusable device, whereas the pump 102 and the handpiece 104 are sterile and disposable.

Figure 3:
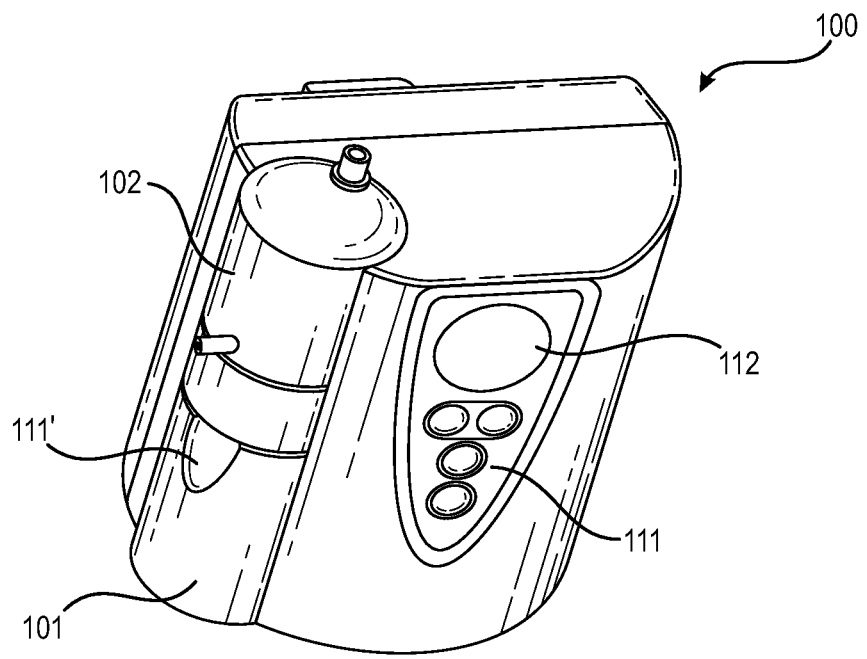
FIG. 3 shows a perspective top front view of the control apparatus of FIG. 2.
Figure 4:
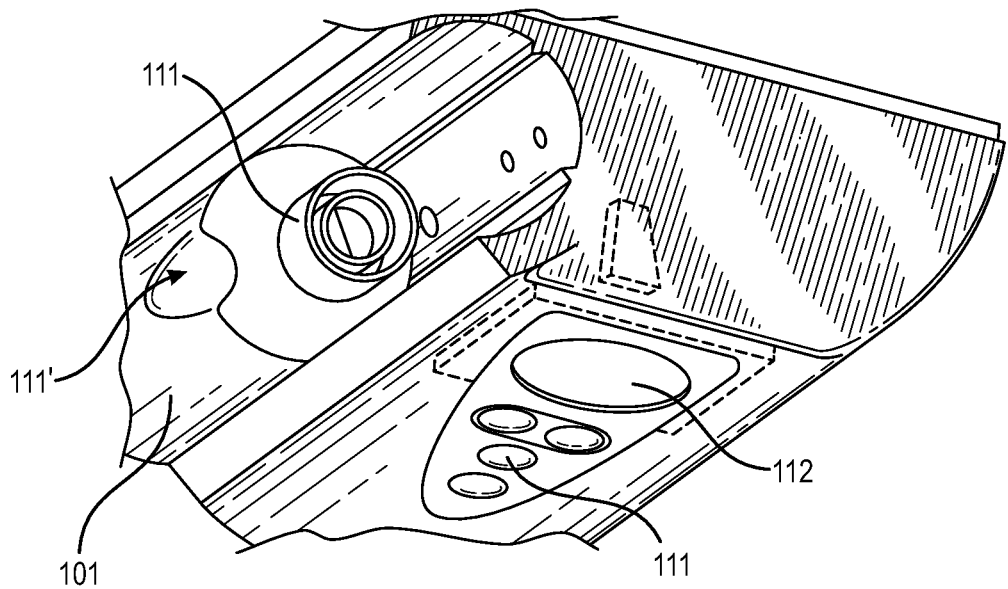
FIG. 4 shows a perspective top front view of a first particular of the control apparatus of FIG. 2, wherein internal components are visible.
Figure 5:
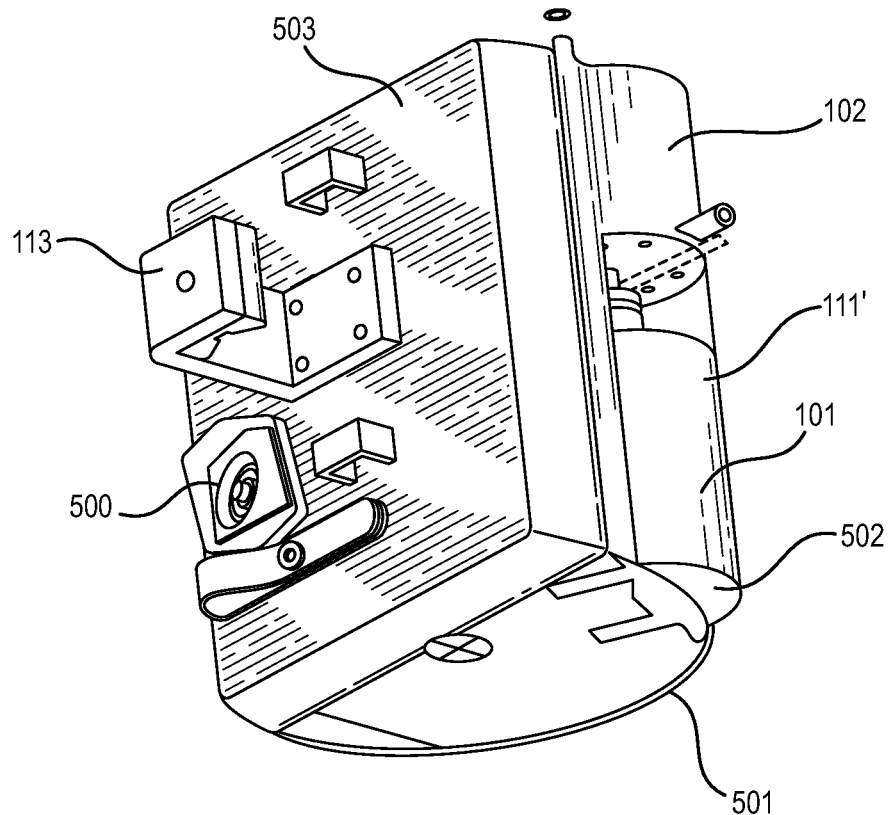
FIG. 5 shows a perspective bottom rear view of the control apparatus of FIG. 2, wherein internal components are visible.
Figure 6:
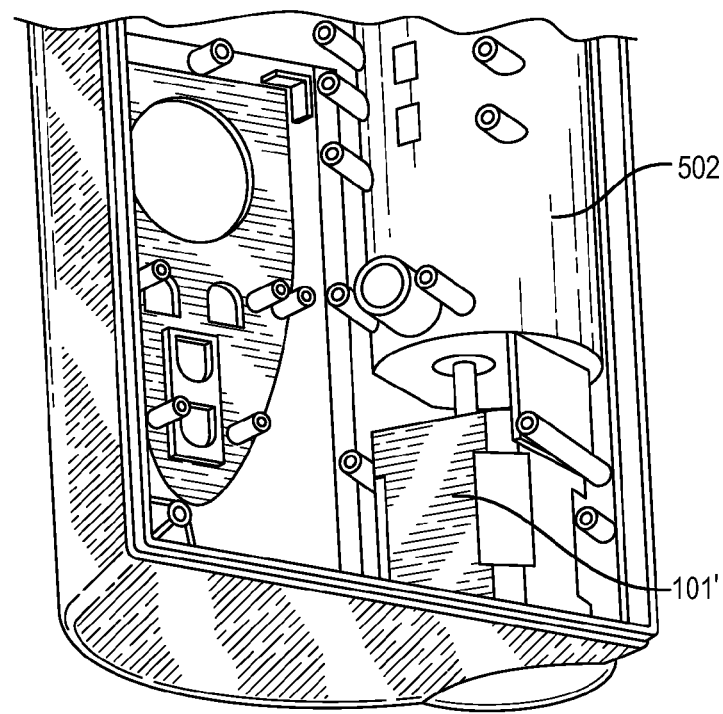
FIG. 6 shows a perspective bottom rear view of a second particular of the control apparatus of FIG. 2.
Figure 7:
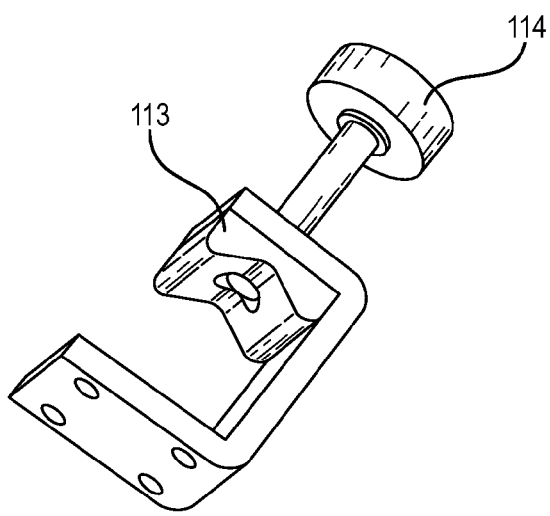
FIG. 7 shows a perspective view of a third particular of the control apparatus of FIG. 2.

With reference to FIGS. 2-6, it may be observed that the control apparatus 100 comprises a substantially cylindrical side slot 101 in which the motor 101' for operating a pump 102 is housed (the pump also comprises all the connection pipes, not shown in FIGS. 2-6) which pump may be stably attached to the slot 101 through a suitable fast coupling 111. In particular, the pump 102, preferably of centrifugal type, is engageable through mechanical guides 111 and tight limit stop snap, whereas a tapered notch 111' on the chassis of the slot 101 aids manual extraction of the pump 102. The control apparatus 100 is capable to be fastened to a hospital metal stand through a suitable rear clamp 113, preferably provided, as shown in FIG. 7, with a clamping handwheel 114. Also three components of the chassis of the apparatus 100 are shown in FIGS. 5 and 6: a front main container 501 (housing, among other things, the electronic boards), a support 502 for the motor-pump assembly, and a rear end cover 503, from which an electric tap 500 for supplying power to the apparatus 100 projects.

Figure 8:
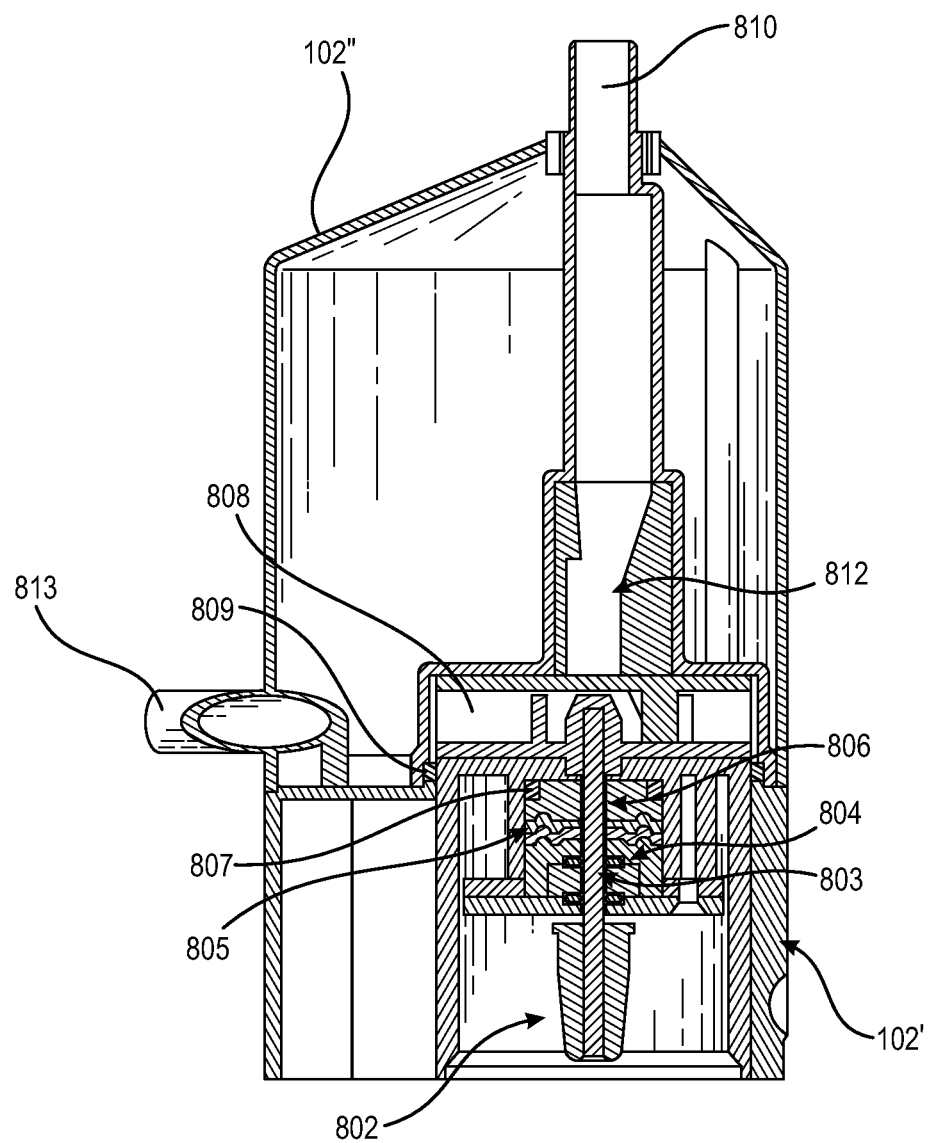
FIG. 8 shows a cross-section view of the pump of the system of FIG. 1.
Figure 9:
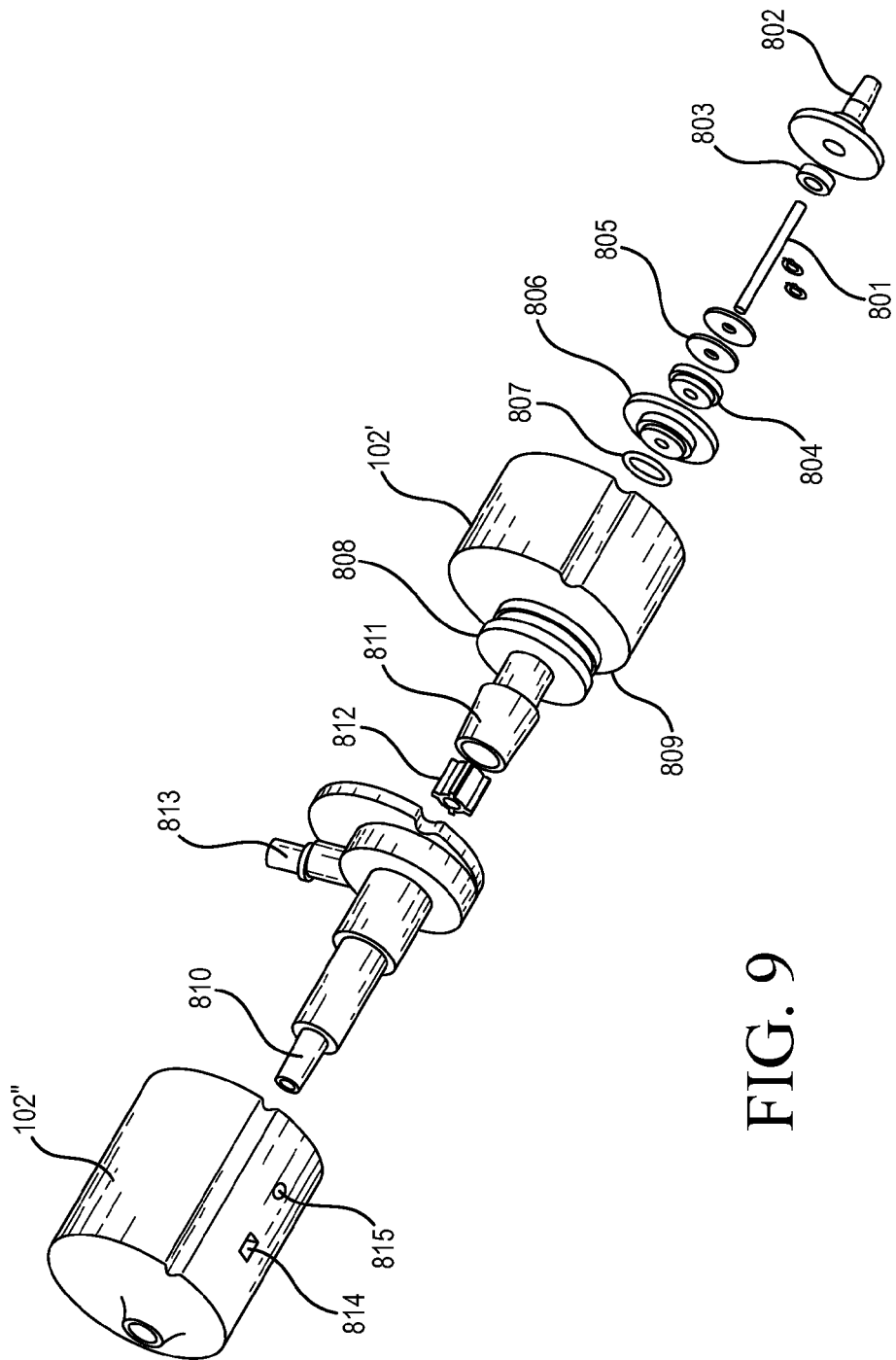
FIG. 9 shows an exploded perspective view of the pump of FIG. 8.
Figure 10:
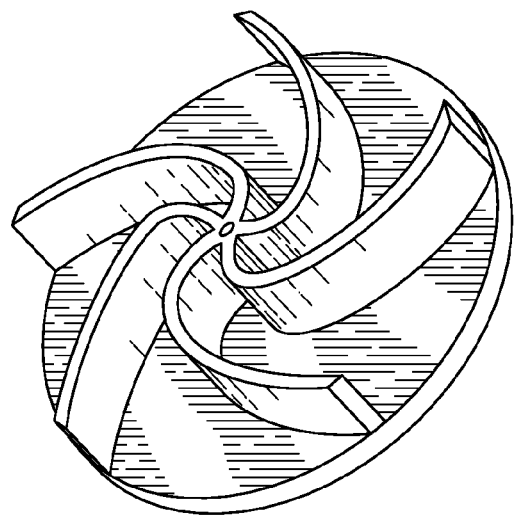
FIG. 10 shows a perspective view of a particular of the pump of FIG. 8.

With reference to FIGS. 8 and 9, it may be observed that the pump 102 comprises a lower pump casing 102' and in an upper pump casing 102". The lower pump casing 102' comprises a spindle 801 to which a male driver 802 (capable to insert in a corresponding female driver directly keyed on the driving shaft) is coupled, a shielded bearing 803 being housed in a suitable support 804 on which tight membranes 805 are applied which separate it from a bush 806, preferably of Teflon, guiding the spindle 801; a first O-ring 807 ensures the tightness of the bush 806. The upper pump casing 102" comprises an impeller 808 (shown in detail in FIG. 10) coupled to the spindle 801, whereas a second O-ring 809 ensures the tightness of the pump 102; in the upper pump casing 102" is further housed a channel 810 for inletting the liquid solution (connectable to an external bag) that houses downwards a bade duct 811 in which a float 812 for sensing presence of liquid in the pump 102 is inserted, which liquid is capable to exit from an outlet channel 813. Finally, two holes 814 and 815 are present on the wall of the upper pump casing 102" for allowing detection by respective optical sensors (illustrated later) with which the apparatus 100 is provided for sensing, respectively, the position of the float 812 (i.e. of the priming state of the pump 102) and the attachment of the pump on the coupling 111.

Figure 11:
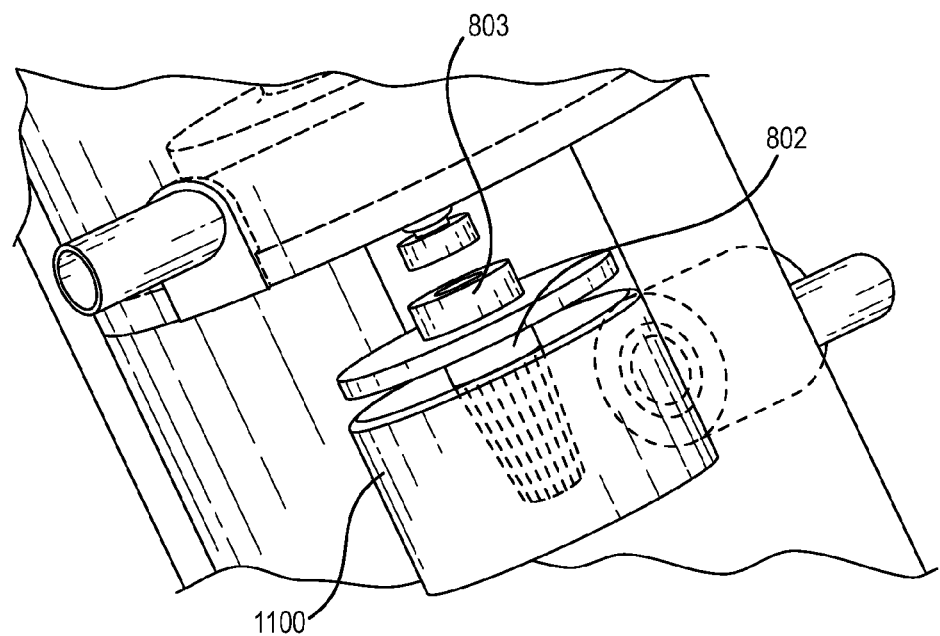
FIG. 11 shows a perspective view of the coaxial bevel gear pair connection of the pump with the motor of the system of FIG. 1.

FIG. 11 shows a particular of the coaxial bevel gear pair connection (comprising male driver 802 and corresponding female driver 1100) of the spindle 801 of the pump 102 with the driving shaft, which connection guarantees a maximum level of system electrical insulation.

Figure 2:
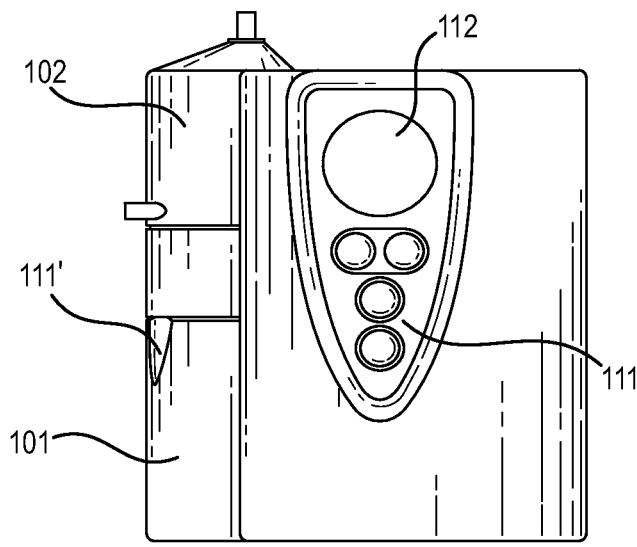
FIG. 2 shows a front view of the control apparatus of the system of FIG. 1.

Still with reference to FIGS. 2-4, it may be observed that the apparatus 100 includes a man-machine interface, or MMI, comprising a keypad 112 and a display 113, the MMI being further provided with three LEDs of different colours, preferably blue, green and red, for signalling the state (not shown in the Figures).

The function of the MMI is to allow the interaction by man, in our case by an operator in operating room, with the system according to the invention. The MMI indicates to the operator, in optical and/or acoustic way, the current state of the irrigation process, and it allows selection of the operation type between continuous and pulsatile, adjustment of parameters such as pump flow rate and, in case of pulse operation, switching times between minimum flow rate and maximum flow rate. In particular, the graphic display 113 shows, in the lower part, a horizontal bar indicating current percentage flow rate (or, in case of pulse operation, current percentage switching frequency) of the pump, and in the upper part it shows the general state of the system (as it will be illustrated later with reference to FIG. 21). Other embodiments of the system according to the invention provide that, through the MMI, it is possible to further set the minimum and maximum rate limits in case of pulse operation.

Figure 12:
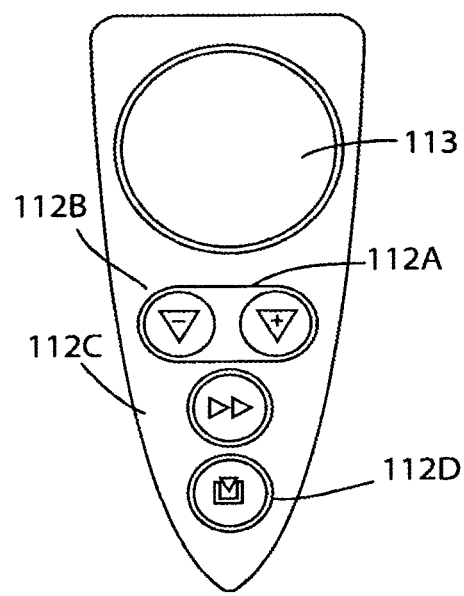
FIG. 12 shows a front view of the display and keypads of the control apparatus of FIG. 2.

As shown in FIG. 12, the keypad 112 comprises four keys 112A, 112B, 112C AND 112D.

The first key 112A, called "UP", allows either the pump flow rate to be increased in case of continuous operation, or the ON and OFF pulse times to be reduced in case of pulse operation (i.e. the switching period to be reduced, increasing the frequency of the same switching).

The second key 112B, called "DOWN", allows either the pump flow rate to be reduced in case of continuous operation, or the ON and OFF pulse times to be increased in case of pulse operation (i.e. the switching period to be increased, reducing the frequency of the same switching).

The third key 112C, called "PULSE", allows selection of the pump operation type. In particular, the operation that is automatically set at power on (default operation) is continuous, i.e. the pump operates in a continuous and uniform way. Pressure on the key PULSE 112C sets the operation in "pulse" mode, that is the pump flow rate is modified at time intervals between a minimum and a maximum, i.e. switching between a minimum flow rate and a maximum flow rate with a switching period; in other words, in pulse operation an alternative passage from the minimum flow rate to the maximum flow rate, and vice versa, occurs (in a Pause-Operation logic, the times of which are variable through the two keys UP 112A and DOWN 112B). If the key PULSE 112C is pressed when the operation has been already switched to pulsatile, the operation returns to continuous mode. The operation mode is visible on the display 113.

The fourth key 112D, called "PRIME", allows to manually require an attempt to prime the pump within a maximum time (time-out), i.e. the pump is activated for a predetermined time, during which if pump priming is not obtained, the pump is automatically stopped and the system passes in a state of failed priming.

As said, the MMI is further provided with three LEDs for signalling the state of the pump 102, preferably of blue, green and red colours, respectively. Depending on the state of the pump, the LEDs turn on as follows: in case of pump not inserted on the coupling 111, all the three LEDs are off; in case of just inserted pump 102, only the blue LED is on; in case of primed pump, only the green LED is on; in case of unprimed pump, only the red LED is on.

Preferably, the MMI further comprises an electroacoustic signaller, or buzzer, that is used both as confirmation of keystroke of a key of the keypad 112 through a beep, and as indication of an alarm state, such as for instance loss of pump priming due to lack of liquid in the bag 109.

For ensuring a sufficient protection from sprinkles, which usually may occur in operating room, all possible ways of penetration of liquids into the chassis of the apparatus 100 are tight sealed. As said, the chassis preferably comprises three components: the front main container 501 (housing, among other things, the electronic boards, the keypad 112, and the display 113), the support 502 for the motor-pump assembly, and the rear end cover 503. The support 502 for the motor-pump assembly is fastened on the front container 501 through a metal bracket plus a sealing along the perimeter of contact between the two parts. The rear cover 503 is fastened to the front container 501 through screws.

Figure 13:
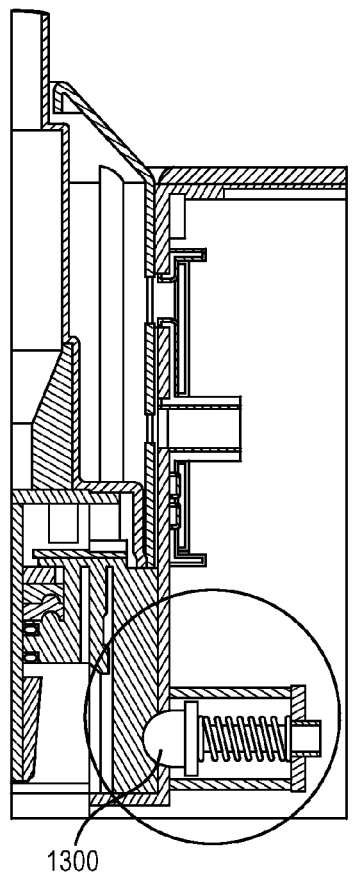
FIG. 13 shows a cross-section partial view of the control apparatus of FIG. 2.
Figure 14:
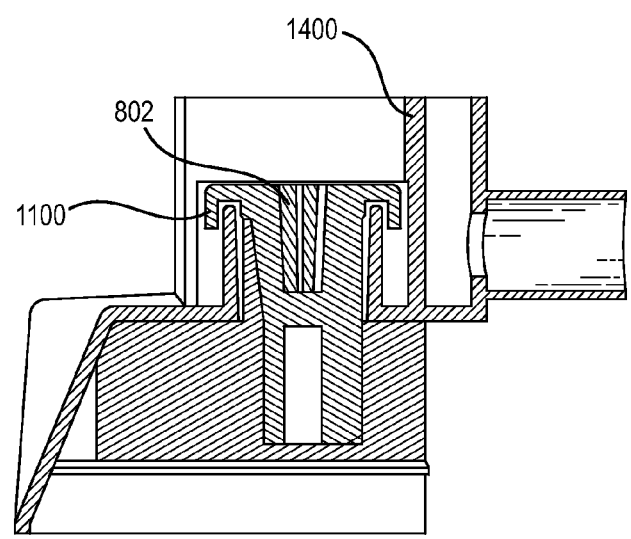
FIG. 14 shows a cross-section view of the coaxial bevel gear pair connection of the pump with the motor of the system of FIG. 1.

Therefore, the chassis has the following possible ways of penetration of liquids which are tight sealed:
line closing rear cover 503 on the front container 501, housing a tight O-ring;
line closing support 502 for the motor-pump assembly on the front container 501, that is sealed with impermeable glue;
holes for fastening the rear clamp 113 to the rear cover 503, closed through insertion of a tight seal with counterflange;
with reference to FIG. 13, hole in the support 502 for the motor-pump assembly for the passage of the snap pin 1300 elastically holding the pump 102, which hole is closed through insertion of a tight seal with counterflange;
holes 814 and 815 in the support 502 for the motor-pump assembly for the optical sensors, closed through insertion of a tight seal with counterflange;
holes and lines closing the keypad 112 and the display 113 on the front container 501, protected by a tight mask made of a thin plate of polycarbonate; and
hole in the support 502 for the motor-pump assembly for the exit of the female driver 1100 of the driving shaft, that is closed by adopting particular geometries, in particular labyrinth seal ones, for the coupling for transmitting the motor torque, as shown in FIG. 14 wherein the significantly tortuous path that a liquid must follow to penetrate inside the support 502 may be observed.

The apparatus 100 comprises electronic boards, on which the electronic circuits are mounted, preferably provided with a processor (or a microcontroller), for controlling the system.

Figure 15A:
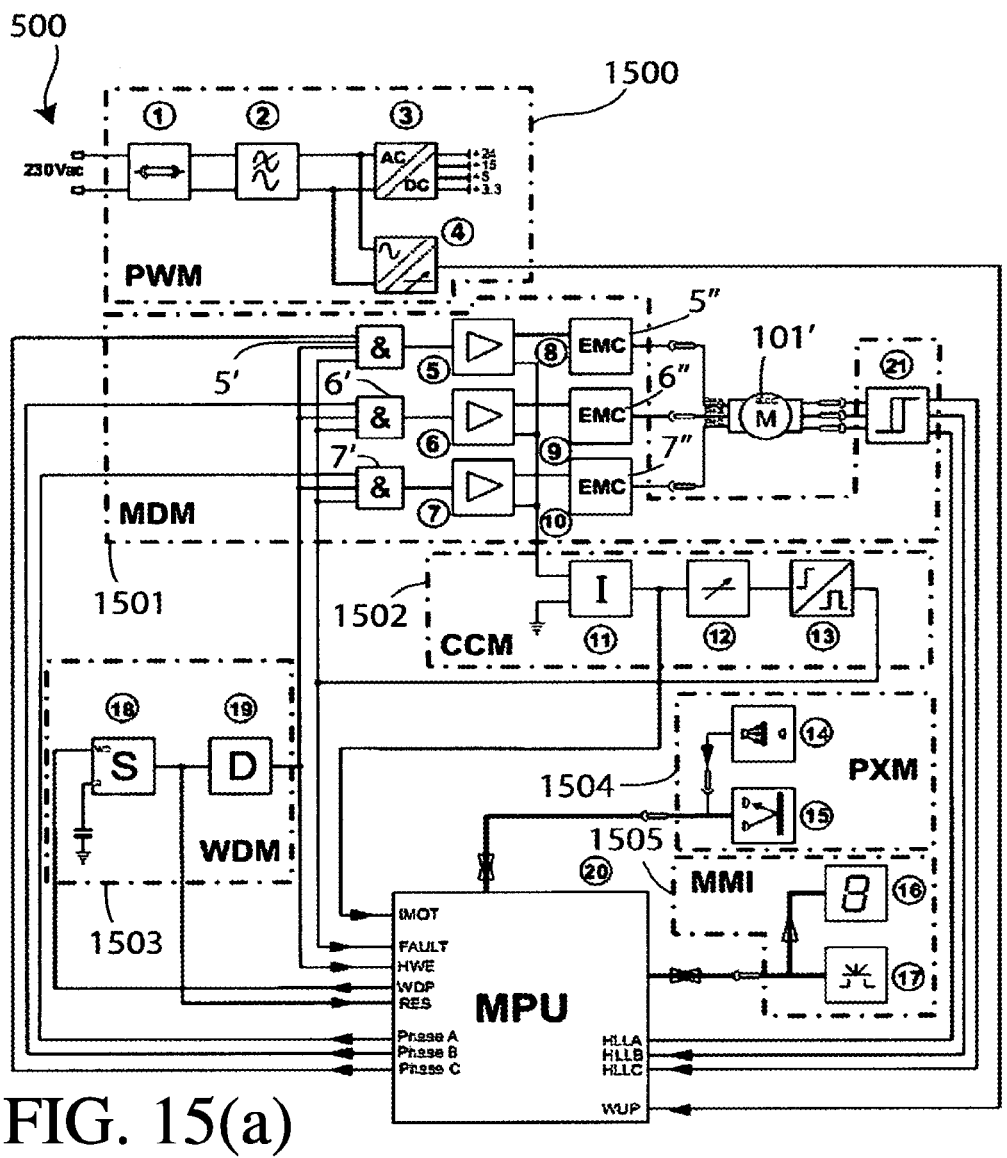
FIG. 15 shows a schematic circuit diagram (FIG. 15a), and a related legend (FIG. 15b) of the electronic circuits of the control apparatus of FIG. 2.
Figure 15B:
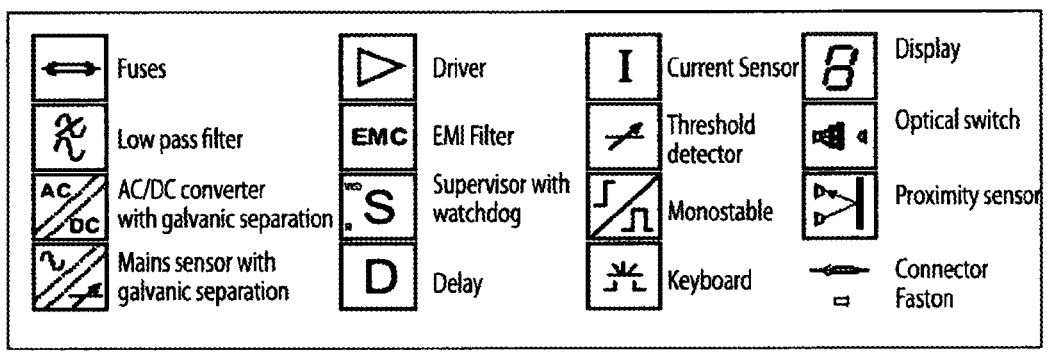

With reference to FIG. 15, a schematic circuit diagram, immediately understandable to those skilled in the art, of the electronic circuits of the apparatus 100 may be observed, supplied by the power supply tap 500, that comprises the following modules controlled by a processor 20: a first module 1500 of power supply (PWM: Power Module); a second module 1501 for driving the motor 101' (MDM: Motor Driver Module); a third module 1502 for controlling the current absorbed by the motor (CCM: Current Control Module); a fourth module 1503 of surveillance (WDM: Watch Dog Module); a fifth module 1504 of proximity detection (PXM: Proximity Module); and a sixth module 1505 of interface (MMI: Man Machine Interface).

The first module PWM 1500 constitutes the power supply section of the whole system and it is of AC/DC conversion type with galvanic insulation of inductive and optical type. The module PWM 1500 may be supplied, through the tap 500, preferably with voltage ranging from 90 to 230 Vac with frequency 50-60 Hz, and it generates all the dc voltages necessary to the operation of the apparatus 100. In particular, the module PWM 1500 comprises a fuse section 1 connected to a low pass filter 2, for the electromagnetic compatibility related to the ducts, in turn connected to an AC/DC converter 3 and to a block 4 for sensing mains with galvanic insulation, which is capable to inform the processor 20 of the occurrence of transients of power down of the apparatus (sending a respective signal to a WUP input of the processor 20), which force the same processor 20 to perform data save and protection subroutines.

The second module MDM 1501 drives the motor 101', that is a three-phase dc low voltage (24 Vdc) BLDC (Brushless Direct Current) motor. The module MDM 1501 comprises a driving circuit (5, 6, 7) for each phase, followed by a respective EMI filter 5", 6" and 7" connected to the corresponding phase of the motor 101'. The phase controls coming from three outputs (Phase A, Phase B, Phase C) of the processor 20 which control the motor 101', before reaching the respective driving circuits 5, 6 and 7, are placed at the input of respective AND gates 5', 6' and 7', along with failure signals described later. In this way, the phase controls may reach and activate the respective driving circuits 5, 6 and 7 only if the failure signals are OFF. Said failure signals come from the modules CCM 1502 and WDM 1503 and they indicate, respectively, an excess of current absorbed by the motor 101' and a hardware breakdown due to malfunction of software or hardware or for lack of mains (power-off). In particular, the processor 20 is capable to generate the phase controls on the basis of three signals received (inputs HLLA, HLLB, HLLC) from a block 21 detecting the position of the rotor comprising three Hall sensors. Moreover, on the basis of such three signals, the processor 20 is further capable to detect an incorrect number of revolutions of the motor 101'.

The third module CCM 1502 carries out the detection of the current absorbed by the motor 101' through a current sensor 11 that converts current in voltage and sends the result towards the processor 20 (input IMOT) for its measurement. Current measurement is used (along with the signals coming from the block 21 of the module MDM) via firmware for controlling the correct operation of the motor 101' and verifying possible failure states. A threshold detector 12, connected before the sensor 11, and a monostable circuit 13, in turn connected before the detector 12, are also part of the same module CCM 1502; in particular, the same detector 12 receives from the sensor 11 the value of the current absorbed by the motor 101', it carries out the continuous control whether current exceeds the allowed maximum current and, in the positive, the monostable circuit 13 inhibits the circuits 5, 6 and 7 driving the motor 101', sending a low signal to the inputs of the AND gates 5', 6', and 7', besides to a corresponding input (FAULT) of the processor 20.

The fourth module WDM 1503 has the function to reset the processor 20 and to inhibit the circuits 5, 6 and 7 driving the motor 101' in case of power-on or firmware malfunction detection. The module WDM 1503 comprises a supervisor block 18 that monitors the power supply voltage and cyclically receives a WD pulse from the processor 20 (output WDP). In case of lack of said pulse within a predetermined time or in case of out-of-tolerance supply voltage, the supervisor block 18 generates a reset signal sent to the processor 20 (input RES) and to a delay block 19 (also belonging to the module WDM 1503). The block 19 behaves as a re-triggerable one-shot multivibrator sending a low signal to the input of the AND gates 5', 6', and 7' (thus inhibiting the circuits 5, 6 and 7 driving the motor 101') and to a corresponding input (HWE) of the processor 20, which signal stops the whole hardware for a time equal to about 2 seconds.

The fifth module PXM 1504 comprises a proximity optical detector 15 and a limit stop optical switcher 14. The optical detector 15 has the function of reading the position of the float 812 of the pump 102 necessary to the system operation, whereas the optical switcher 14 is used as sensor of presence of the pump 102 on the coupling 111 on the slot 101 of the motor 101'.

The sixth module MMI 1505 of interface comprises the graphic display 113, preferably a 128×128 pixel one, and the keypad 112 with four keys, which allow an operator to program and control the system operation.

Figure 16:
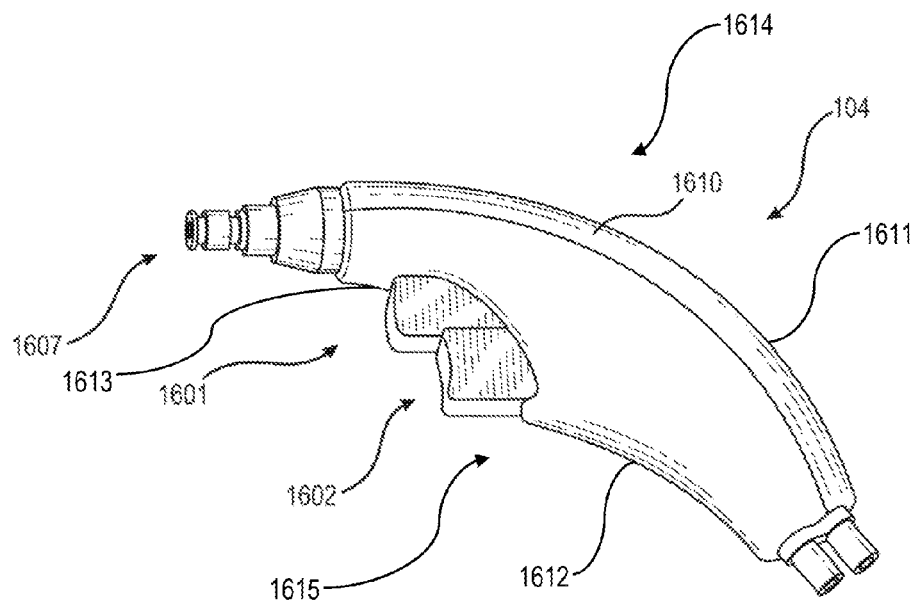
FIG. 16 shows a perspective view of the handpiece of the system of FIG. 1.
Figure 17:
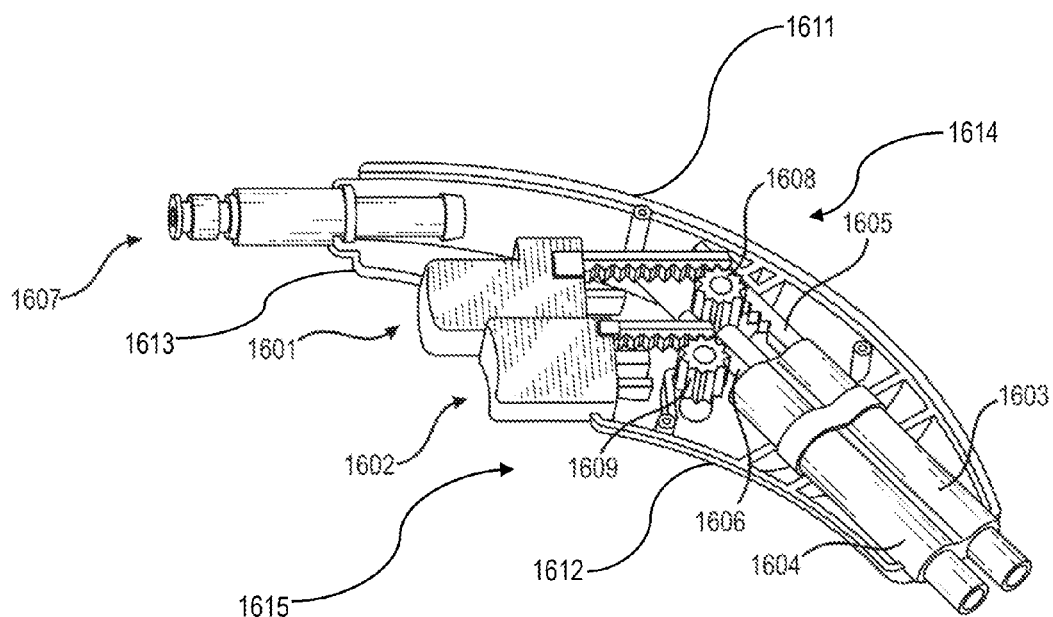
FIG. 17 shows a view of internal components of the handpiece of FIG. 16.
Figure 18:
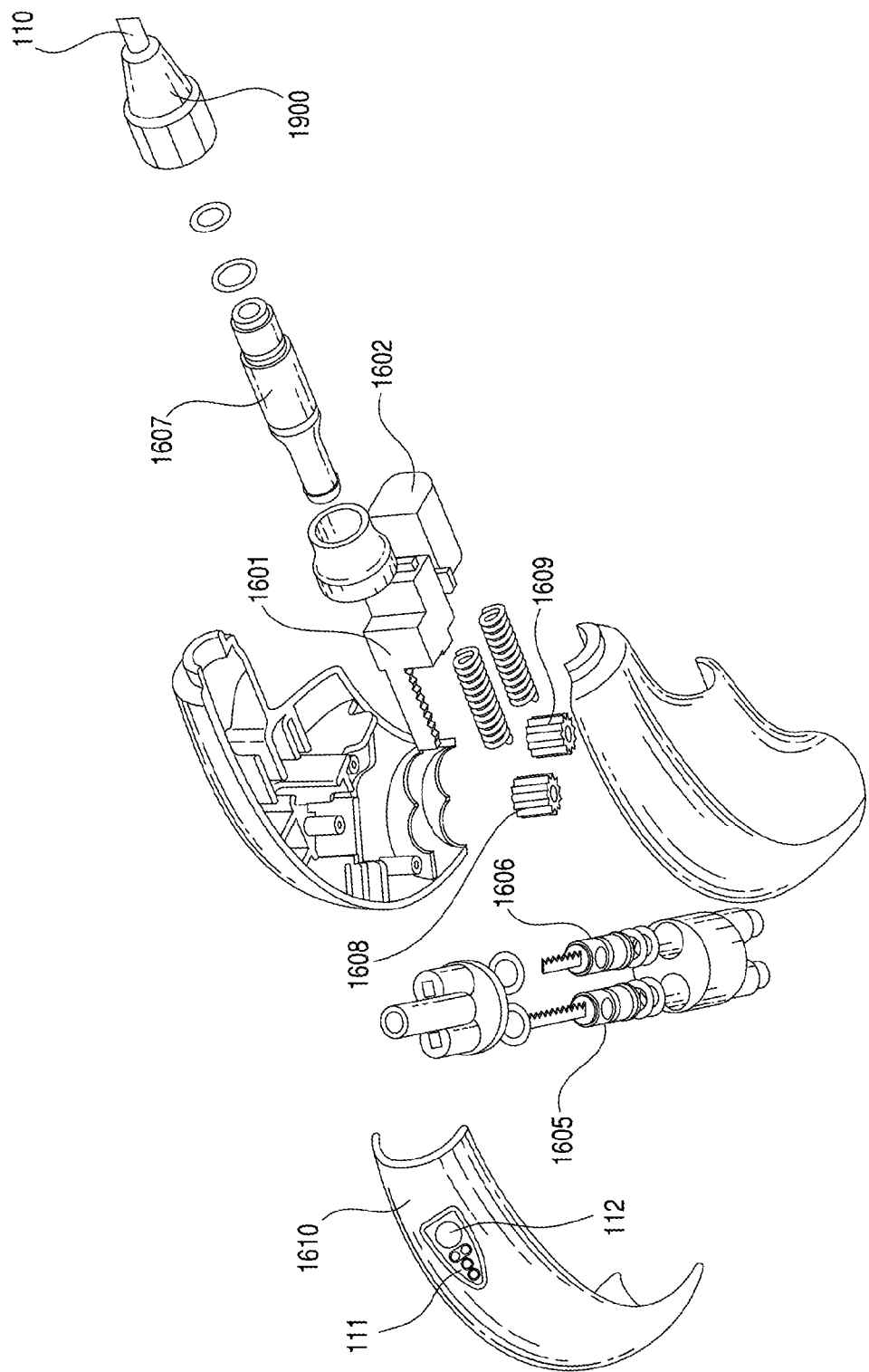
FIG. 18 shows an exploded perspective view of the handpiece of FIG. 16 and of the probe of the system of FIG. 1.

With reference to FIGS. 16-18, it may be observed that the handpiece 104 is the part handled by the surgeon allowing, through an irrigation button 1601 and a suction button 1602, to control the operation of two corresponding valves, respectively an irrigation one 1603 and a suction one 1604 (preferably integrally coupled to each other) in which corresponding shutters, respectively 1605 and 1606, slide, which in turn regulate the irrigation and suction phases through a steel probe 110 (shown in FIGS. 1 and 18) provided with a probe holder 1900 (shown in detail in FIGS. 18 and 19) that connects by snap connection to a fast coupling nozzle 1607 of the handpiece 104. The inlets of the valves 1603 and 1604 must be connected to respective irrigation and suction pipes (indicated with the reference numbers 103 and 106 in FIG. 1).

In particular, motion of each button, 1601 or 1602, is transmitted to the corresponding shutter, 1605 or 1606, through a respective gear-rack transmission. In fact, both the buttons 1601 and 1602 and the shutters 1605 and 1606 are provided with end racks engaging two respective gear wheels 1608 and 1609 rotatably coupled to the chassis of the handpiece 104.

The handpiece top is provided with an anti-skidding coating 1610, preferably of Laprene®.

Moreover, as shown in FIGS. 16-17, the form of the handpiece 104, is an ergonomic banana shape with a first elongated arcuate surface 1611 extending from the two valves 1603 and 1604 to the output nozzle 1607, and defines a proximal face 1614 of the handpiece 104. Handpiece 104 also includes a second elongated arcuate surface 1612, spaced from the first elongated arcuate surface 1611, extending from the two valves 1603 and 1604 towards the output nozzle 1607. Handpiece 104 also includes a third elongated arcuate surface 1613, spaced from the first elongated arcuate surface 1611, extending from the output nozzle 1607 towards the second elongated arcuate surface 1612. As further shown in FIGS. 16-17, the second and third elongated arcuate surfaces 1612 and 1613 are disposed on the same side and defines a distal face 1615 of the handpiece 104. Handpiece 104 also includes a pair of buttons 1601 and 1602 contiguous with each other and are both disposed adjacent to each other on the distal face 1615 of the handpiece 104 between the second and the third elongated arcuate surface 1612 and 1613. The pair of buttons 1601 and 1602 control the operation of the two valves 1603 and 1604. When the pair of buttons 1601 and 1602 are pressed, the two valves 1603 and 1604 communicate with the output nozzle 1607. The ergonomic banana shape of handpiece 104 allows a comfortable and firm grip by an operator both when it is placed with the nozzle 1607 above the four fingers of the hand different from the thumb (i.e. when the handpiece 104 is handled as a pistol with the inlets of the valves 1603 and 1604 below the hand), and when it is placed with the nozzle 1607 below such four fingers (i.e. when it is in overturned position with the inlets of the valves 1603 and 1604 above the hand). To this end, the surfaces of the buttons 1601 and 1602 on which the operator's fingers (preferably index and middle fingers in the pistol-like grip and vice versa in the overturned grip) exert a pressure are respectively convex and concave.

It must be noted that it is possible to simultaneously control the shutters 1605 and 1606 to open (by simultaneously pressing the related buttons 1601 and 1602) towards the outlet nozzle 1607. Even if this would occur during system operation, this causes the direct canalisation of the irrigation line towards the suction line, and hence the probe would be at a pressure only slightly different from the ambient pressure whereby such situation does not constitute a danger for the patient.

Other embodiments of the system according to the invention may provide that control keys, similar to those of the keypad 112, (and possibly a display and/or signalling LEDs and/or a buzzer) are present on the handpiece 104 for allowing to control the operation of the apparatus 100 directly from the handpiece 104. The control signals may be sent from the handpiece 104 to the processor 20 (and possibly vice versa) by wired or wireless connection, e.g. through radio frequency or infrared connection.

It must be noted that the handpiece 104 is also applicable to irrigation and suction systems comprising control apparatuses different from the one of the system according to the present invention.

In order to better understand the present invention, the operating modes of the preferred embodiment of the system according to the invention will be described in the following, similar modes being valid for the other embodiments.

As shown in FIG. 1, the apparatus 100 fastens, through the clamp 113, to a hospital metal stand 105 under the bag 109 of physiological liquid, that is also hung on the top of the stand 105. Once fastened, the apparatus 100 is supplied by connecting the power supply tap 500 to the mains, preferably at 230 Vac. In this condition, the apparatus 100 is in a stand-by state indicated by both the display 113 and the signalling LEDs, all off, indicating that no pump has been inserted yet.

At this point a pump 102 is inserted, the handpiece 104 provided with probe 110 is coupled to the pump 102 through the irrigation pipe 103, the infusion pipe 107 of the pump 102 is inserted into the bag 109 of liquid through the spike 108 and the suction pipe 106 coming from the handpiece 104 is connected to the point at negative pressure present in the operating room. For a correct and safe operation, it is necessary that the bag 109 is placed above the apparatus 100 using all the available length of the infusion pipe 107, whereas the suction pipe 106 must be connected to the operating room suction system provided for the normal surgical aspirators interposing a reservoir for collecting liquids with adequate capacity in relation to the foreseen needs.

The apparatus 100 checks the presence of the pump 102 and passes in the pre-priming state indicated by both the display 113 and turning-on of the signalling blue LED.

The subsequent step is to prime the pump 102. To this end, an operator presses the irrigation button 1601 on the handpiece 104, the liquid begins to flow by gravity through the pump 102 until it exits from the steel probe 110. When a sufficient quantity of liquid has flowed by gravity from the probe 110, the operator releases the irrigation button 1601, and the apparatus 100 checks the presence of liquid in the hydraulic circuit and passes in the primed pump state, indicated by both the display 113 and turning-on of the signalling green LED.

Once the priming state has been reached, whenever the surgeon presses the irrigation button 1601, the apparatus 100 checks and activates the pump 102 that pushes the liquid towards the handpiece 104. The pump 102 automatically stops when the irrigation button 1601 is released.

The first loss of priming due to the exhaustion of the physiological liquid in the bag 109 or to any anomaly is detected by the apparatus 100 that stops the pump 102 and indicates the state of unprimed pump 102 on the display 113, with simultaneous turning-on of the signalling red LED.

The new priming of the pump 102 occurs manually through pressure of the key PRIME 112D of the keypad 112 of the apparatus 100, after either the cause of the anomaly has been removed or the bag 109 of liquid has been replaced.

As said before, the surgeon may set the operating functions through the keypad 112, whereas the display 113 shows the information on the system state.

Figure 20:
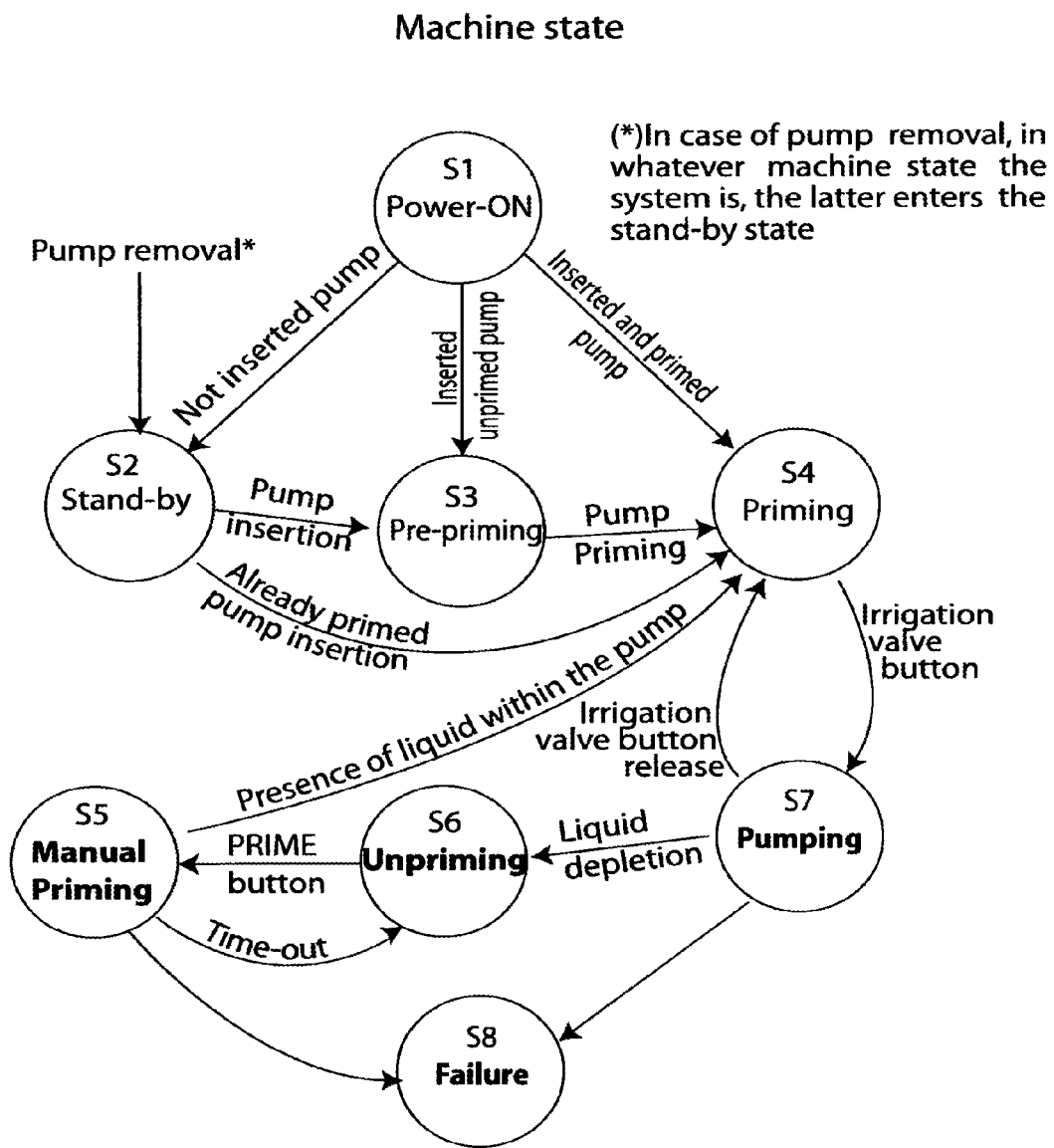
FIG. 20 schematically shows the machine states of the control apparatus of FIG. 2.

FIG. 20 schematically shows the eight machine states of the apparatus 100, according to which the electronics operates, whereas FIG. 21 shows the graphic information displayed by the display 113.

At power-on, the apparatus 100 is in the first state S1 (Power-ON). In such state, the apparatus 100 performs a test for analysing whether the pump 102 is inserted in the coupling 111 and whether it is primed or not. Depending on the result of the test, the apparatus enters one of three subsequent machine states S2, S3 or S4.

Figure 21A:
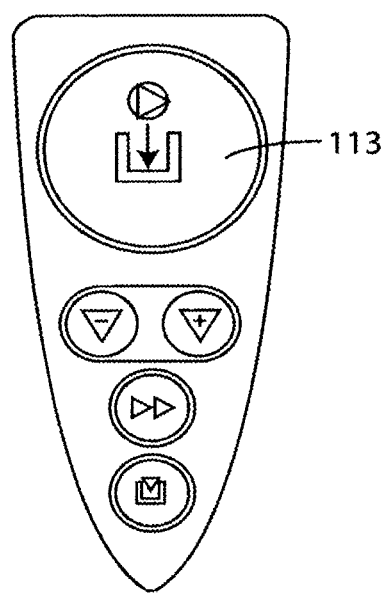
FIG. 21 shows graphical information displayed by the display of FIG. 12 in the various machine states of the control apparatus of FIG. 2.

The second state S2 (Stand-by) is the state in which the apparatus 100 is immediately after having been supplied in the case where the pump 102 has not yet been inserted, or after that the pump 102 has been disconnected starting from any operation condition. FIG. 21a shows the display 113 in state S2.

Figure 21B:
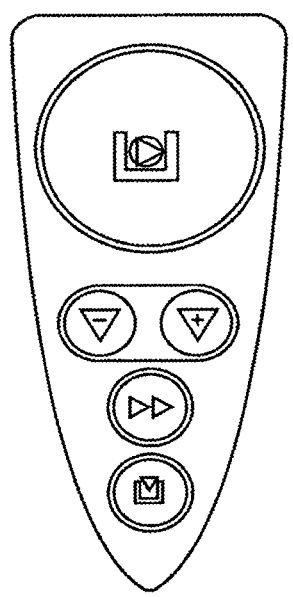

The third state S3 (Pre-priming) is the state in which the apparatus 100 is immediately after having been supplied in the case where the pump 102 has been already inserted prior to applying the power supply, but it is not yet primed (i.e. in the condition of no liquid within the pump 102), or an unprimed pump 102 has been inserted with the apparatus 100 in stand-by state S2. FIG. 21b shows the display 113 in state S3.

Figure 21C:
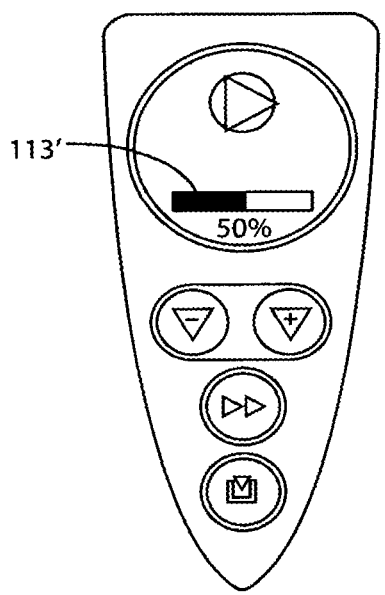
Figure 21D:
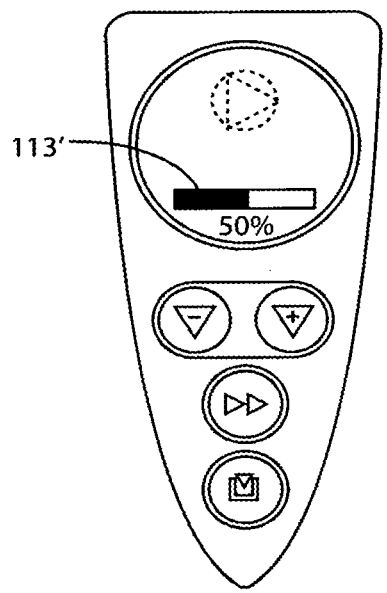

The fourth state S4 (Priming) is the state indicating that the pump 102 is ready to pump since it is already charged with liquid. In the case where a new pump 102 is coupled in the apparatus 100 and it is connected to the bag 109 of solution, it is necessary to provide for its priming by opening the irrigation valve 1603 on the handpiece 104 and making an adequate quantity of liquid flow by gravity. In this state S4 it is possible to modify the flow rate of the pump 102 through the keys 112A and 112B of the keypad 112, and to set the operation type by selecting it between continuous and pulsatile through the key 112C. FIGS. 21c and 21d show the display 113 in state S4 with operation, respectively, continuous and pulsatile, wherein the bar 113' signalling the flow rate (or the frequency, in case of pulse operation) is visible.

Figure 21E:
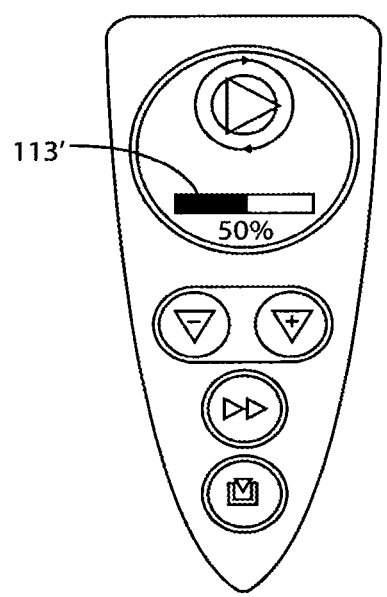
Figure 21F:
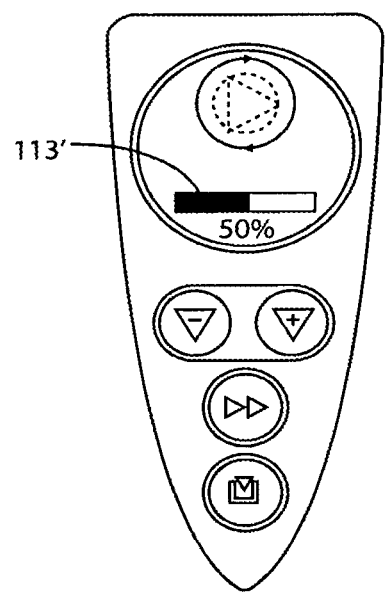

Pumping state S7 is the state with which the irrigation function is obtained and it is reached by the apparatus 100 when the button 1601 opening the irrigation valve 1603 on the handpiece 104 is pressed. In this state S7 the pump 102 is active and the operator may modify the flow rate of the pump 102 (through the keys 112A and 112B of the keypad 112) and he may set the operation type between continuous and pulsatile (through the key 112C). FIGS. 21e and 21f show the display 113 in state S7 with continuous and pulsatile, respectively, operation, wherein the bar 113' signalling the flow rate (or the frequency) is visible.

Figure 21G:
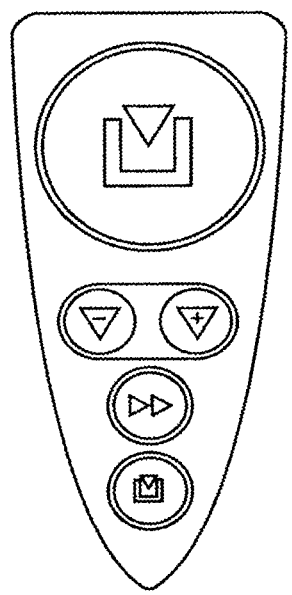

Unpriming (i.e. loss of priming, possibly during pumping, i.e. "end of liquid") state S6 is the state in which the apparatus 100 arrives when the pump 102 has lost its priming, i.e. when a lack of liquid in the pump 102 occurs. The cause is normally due to the exhaustion of the liquid in the bag 109. In this state S6 is also activated the alarm buzzer. FIG. 21g shows the display 113 in state S6.

Figure 21H:
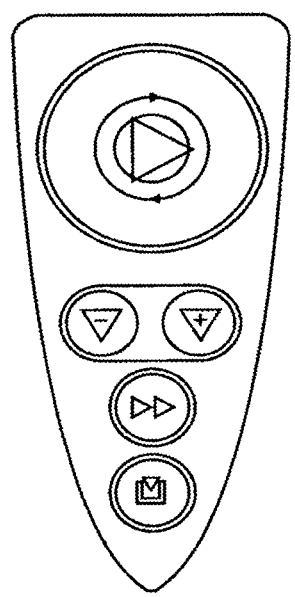

Manual Priming state S5 is the state in which the apparatus 100 arrives in the case where it fails to automatically prime and the key 112D PRIME is pressed for manually forcing an attempt of priming the pump 102 with time-out. If in the predetermined time the priming of the pump 102 is not obtained, the latter is automatically stopped and the apparatus 100 passed in Unpriming state S6. FIG. 21h shows the display 113 in state S5.

Figure 21I:
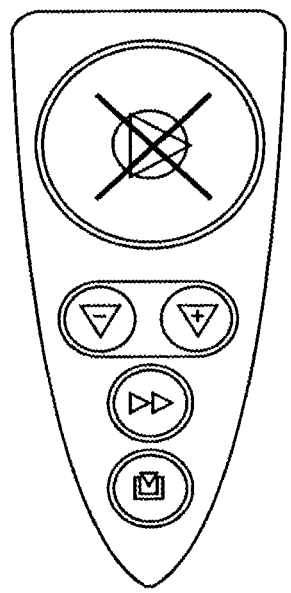

Finally, Failure state S8 occurs when the control processor 20 detects an incorrect number of revolutions of the motor 101' or an excessive current load, beyond the nominal operation threshold. State S8 corresponds to a malfunction of mechanical type that may be induced by a plurality of factors, such as for instance the stop of the impeller 808 of the pump 102, or a failure of the electric motor 101' implying a loss of revolutions, thus not ensuring an adequate flow rate. FIG. 21i shows the display 113 in state S8.

The preferred embodiments have been above described and some modifications of this invention have been suggested, but it should be understood that those skilled in the art can make variations and changes, without so departing from the related scope of protection, as defined by the following claims.

The invention claimed is:

1. An irrigation and suction system, in particular for laparoscopic surgery, comprising:
   an active control apparatus, provided with a reusable motor attached to and operating a disposable pump, and
   a disposable handpiece provided with two valves capable to be connected respectively to an output duct from the pump and to a suction line, the two valves being operatable for making respectively the pump and the suction line communicate with a single output nozzle of the handpiece, the nozzle being capable to support a probe, the active control apparatus comprising controlling electronics means for driving the motor, wherein the irrigation and suction system comprises interface means connected to said controlling electronics means capable to select an operation mode of the motor between a continuous mode, wherein the pump delivers a fluid in a continuous and uniform way, and a pulse mode, wherein the pump flow rate switches between a minimum flow rate and a maximum flow rate with a switching period, the interface means comprising a keypad with keys suitable to allow to select the operation mode of the motor, wherein the interface means also comprises a graphic display suitable to visualize an operation state of the irrigation and suction system and a man-machine interface electronic module to which said keys and said graphic display are connected, and the interface means are housed on a handpiece, and wherein the handpiece has an ergonomic banana shape with a first elongated arcuate surface extending from the two valves to the output nozzle on a proximal face of the handpiece, a second elongated arcuate surface spaced from the first elongated arcuate surface and extending from the two valves towards the output nozzle, a third elongated arcuate surface extending from the output nozzle towards the second elongated arcuate surface, a pair of buttons which are contiguous with each other and are both disposed adjacent to each other on a distal face of the handpiece between the second and the third elongated arcuate surfaces, wherein the pair of buttons controls the operation of the two valves, whereby when the pair of buttons is pressed the two valves may communicate with the output nozzle.

2. The system of claim 1, wherein said interface means is capable to further select a flow rate of the pump.

3. The system of claim 1, wherein said interface means is capable to further select, in case of pulse operation, one or more parameters selected from a group comprising of a minimum flow rate, a maximum flow rate, and a switching period.

4. The system of claim 1, wherein said interface means comprises a keyboard.

5. The system of claim 4, wherein said interface means comprises one or more elements selected from the group comprising a light signaling LED and an electro-acoustic indicator, or a buzzer.

6. The system of claim 1, wherein said interface means is connected to said controlling electronics means through a cable or a wireless connection.

7. The system of claim 1, wherein the active control apparatus comprises a detecting means, connected to said controlling electronics means and capable to detect a priming state of the pump, whereby said controlling electronics means enables or disables driving the motor when said detecting means detects that the pump is, respectively, primed or unprimed.

8. The system of claim 7, wherein said detecting means is capable to detect an attaching of the pump to the motor, whereby said controlling electronics means enables or disables driving the motor when said detecting means detects that a pump is, respectively, attached or not attached.

9. The system of claim 7, wherein said interface means is further capable to cause an attempt of priming the pump within a maximum period (time-out), whereby the pump is operated for a pre-established period.

10. The system of claim 1, wherein the active control apparatus comprises a current detecting means connected to said controlling electronics means capable to detect a current absorbed by the motor.

11. The system of claim 10, wherein said current detecting means is capable to further detect when said current absorbed by the motor exceeds a maximum threshold value.

12. The system of claim 11, wherein said current detecting means directly inhibits said electronics means for driving the motor when it detects that said current absorbed by the motor exceeds said maximum threshold value.

13. The system according to claim 10, wherein said controlling electronics means is capable to detect an unpriming state of the pump on a basis of the current absorbed by the motor as detected by said current detecting means, whereby said controlling electronics means enables or inhibits driving the motor when it detects that the pump is respectively primed or unprimed.

14. The system according to claim 10, wherein said controlling electronics means is capable to detect a number of revolutions of the motor, whereby it inhibits driving the motor when said number of revolutions of the motor is incorrect.

15. The system according to claim 1, wherein the active control apparatus comprises a watching means connected to said controlling electronics means, said watching means being capable to detect one or more conditions selected from a group comprising a power-on state of the active control apparatus, a malfunction signaled by said controlling electronics means, an insufficient power supply, whereby the watching means resets said controlling electronics means or inhibits driving the motor for at least a time period upon detection of said one or more conditions.

16. The system according to claim 1, wherein an attaching between the motor and the pump is of coaxial bevel gear pair type, comprising a male driver and a corresponding female driver.

17. The system according to claim 16, wherein the attaching between the motor and the pump is arranged according to a labyrinth type geometry seal.

* * * * *